United States Patent [19]
Hill

[11] Patent Number: 6,028,091
[45] Date of Patent: Feb. 22, 2000

[54] MEDICAMENT

[75] Inventor: James Hill, Brentford, United Kingdom

[73] Assignee: SmithKline Beecham plc, Middlesex, United Kingdom

[21] Appl. No.: 09/371,673

[22] Filed: Aug. 10, 1999

Related U.S. Application Data

[62] Continuation of application No. 09/277,922, Mar. 29, 1999, abandoned, which is a continuation of application No. 08/901,460, Jul. 28, 1997, abandoned, which is a continuation of application No. 08/732,027, Oct. 16, 1996, abandoned, which is a continuation of application No. 08/535,796, Sep. 28, 1996, abandoned, which is a continuation of application No. 08/375,028, Jan. 19, 1995, abandoned, which is a continuation of application No. 08/074,870, filed as application No. PCT/GB91/02220, Dec. 12, 1991, abandoned.

[30] Foreign Application Priority Data

Dec. 14, 1990 [GB] United Kingdom ................ 9027210

[51] Int. Cl.[7] .................... A61K 31/41; A61K 31/415
[52] U.S. Cl. .................. 514/381; 514/382; 514/397; 514/398; 514/399; 514/400
[58] Field of Search ................ 514/381, 382, 514/397, 398, 399, 400

[56] References Cited

U.S. PATENT DOCUMENTS

| | | | |
|---|---|---|---|
| 5,015,651 | 5/1991 | Carini et al. | 514/381 |
| 5,043,349 | 8/1991 | Carini et al. | 514/427 |
| 5,064,825 | 11/1991 | Chakravarty et al. | |
| 5,081,127 | 1/1992 | Carini et al. | 514/359 |
| 5,185,351 | 2/1993 | Finkelstein et al. | |
| 5,312,828 | 5/1994 | Finkelstein et al. | |
| 5,336,677 | 8/1994 | Sarantakis et al. | |
| 5,376,666 | 12/1994 | Duncia. | |

FOREIGN PATENT DOCUMENTS

| | | |
|---|---|---|
| 0 323 841 A1 | 5/1989 | European Pat. Off. |
| 0 403 158 A2 | 7/1990 | European Pat. Off. |
| 0 403 159 A2 | 7/1990 | European Pat. Off. |
| WO 91/14367 | 3/1991 | WIPO. |
| 9210182 | 6/1992 | WIPO. |

*Primary Examiner*—Deborah C. Lambkin
*Attorney, Agent, or Firm*—Mary E. McCarthy; Stephen Venetianer; Charles M. Kinzig

[57] ABSTRACT

The present invention relates to the use of an angiotensin II receptor antagonist in the manufacture of a medicament for the treatment of diabetic nephropathy.

11 Claims, No Drawings

MEDICAMENT

This is a continuation of application Ser. No.: 09/277,922 filed Mar. 29, 1999 abandoned, which is a continuation of application Ser. No. 08/901,460 filed Jul. 28, 1997, abandoned, which is a continuation of application Ser. No. 08/732,027, filed Oct. 16, 1996, now abandoned, which is a continuation of application Ser. No. 08/535,796, filed Sep. 28, 1996, now abandoned, which is a continuation of application Ser. No. 08/375,028, filed Jan. 19, 1995, now abandoned, which is a continuation of application Ser. No. 08/074,870, filed Jun. 10, 1993, abandoned, which is a 371 of PCT/GB91/02220 filed Dec. 12, 1991.

FIELD OF THE INVENTION

The present invention relates to therapeutic agents that are angiotensin II (AII) receptor antagonists useful in the treatment of diabetic nephropathy.

BACKGROUND OF THE INVENTION

Interruption of the renin-angiotensin system (RAS) with converting enzyme inhibitors, such as captopril, has proved clinically useful in the treatment of certain disease states, such as hypertension and congestive heart failure [Abrams, et al., *Federation Proc.*, 43:1314 (1984)]. Furthermore, evidence suggests that inhibition of this system may be beneficial in treating diabetic nephropathy. Since AII is the biologically active component of the renin-angiotensin system responsible for the system's peripheral effects, the most direct approach towards inhibition of RAS and in particular AII-induced diabetic nephropathy would be blockade of angiotensin II at its receptor.

SUMMARY OF THE INVENTION

The present invention provides a new method of treatment of diabetic nephropathy in a mammal which comprises administering to a subject in need thereof an effective non-toxic amount of an angiotensin II receptor antagonist.

The present invention also provides for the use of an angiotensin II receptor antagonist in the manufacture of a medicament for the treatment of diabetic nephropathy.

DESCRIPTION OF THE INVENTION

The present invention is a therapeutic method for treating diabetic nephropathy in mammals. The method utilizes a class of antagonists which have been previously prepared and evaluated as effective AII receptor antagonists. Examples of suitable angiotensin II receptor antagonists include, but are not limited to, the following:

Substituted imidazoles of the formula (I), which are described in U.S. application Ser. No. 07/746,262, filed Aug. 14, 1991:

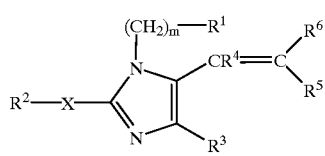

(I)

in which:

$R^1$ is adamantyl, phenyl, biphenyl, or naphthyl, with each aryl group being unsubstituted or substituted by one to three substituents selected from Cl, Br, F, I, $C_1$–$C_6$alkyl, nitro, A-$CO_2R^7$, tetrazol-5-yl, $C_1$–$C_6$alkoxy, hydroxy, $SC_1$–$C_6$alkyl, $SO_2NHR^7$, $NHSO_2R^7$, $SO_3H$, $CONR^7R^7$, CN, $SO_2C_1$–$C_6$alkyl, $NHSO_2R^7$, $PO(OR^7)_2$, $NR^7R^7$, $NR^7COH$, $NR^7COC_1$–$C_6$alkyl, $NR^7CON(R^7)_2$, $NR^7COW$, W, $SO_2W$;

m is 0–4;

$R^2$ is $C_2$–$C_{10}$alkyl, $C_3$–$C_{10}$alkenyl, $C_3$–$C_{10}$alkynyl, $C_3$–$C_6$cycloalkyl, or $(CH_2)_{0-8}$phenyl unsubstituted or substituted by one to three substituents selected from $C_1$–$C_6$alkyl, nitro, Cl, Br, F, I, hydroxy, $C_1$–$C_6$alkoxy, $NR^7R^7$, $CO_2R^7$, CN, $CONR^7R^7$, W, tetrazol-5-yl, $NR^7COC_1$–$C_6$alkyl, $NR^7COW$, $SC_1$–$C_6$alkyl, $SO_2W$, or $SO_2C_1$–$C_6$alkyl;

X is a single bond, S, $NR^7$, or O;

$R^3$ is hydrogen, Cl, Br, F, I, CHO, hydroxymethyl, $COOR^7$, $CONR^7R^7$, $NO_2$, W, CN, $NR^7R^7$, or phenyl;

$R^4$ and $R^5$ are independently hydrogen, $C_1$–$C_6$alkyl, thienyl-Y-, furyl-Y-, pyrazolyl-Y-, imidazolyl-Y-, pyrrolyl-Y-, triazolyl-Y-, oxazolyl-Y-, isoxazolyl-Y-, thiazolyl-Y-, pyridyl-Y-, or tetrazolyl-Y-, except that $R^4$ and $R^5$ are not both selected from hydrogen and $C_1$–$C_6$alkyl and each heterocyclic ring is unsubstituted or substituted by $C_1$–$C_6$alkyl, $C_1$–$C_6$alkoxy, Cl, Br, F, I, $NR^7R^7$, $CO_2R^7$, $SO_2NHR^7$, $SO_3H$, or $CONR^7R^7$, OH, $NO_2$, W, $SO_2W$, $SC_1$–$C_6$alkyl, $SO_2C_1$–$C_6$alkyl, $NR^7COH$, $NR^7COW$, or $NR^7COC_1$–$C_6$alkyl;

Y is a single bond, O, S, or $C_1$–$C_6$alkyl which is straight or branched or optionally substituted by phenyl or benzyl, wherein each of the aryl groups is unsubstituted or substituted by halo, $NO_2$, $CF_3$, $C_1$–$C_6$alkyl, $C_1$–$C_6$alkoxy, CN, or CO $R^7$;

$R^6$ is —Z—$COOR^8$ or —Z—$CONR^7R^7$;

Z is a single bond, vinyl, —$CH_2$—O—$CH_2$—, methylene optionally substituted by $C_1$–$C_6$alkyl, one or two benzyl groups, thienylmethyl, or furylmethyl, or —C(O)NHCHR$^9$—, wherein $R^9$ is H, $C_1$–$C_6$alkyl, phenyl, benzyl, thienylmethyl, or furylmethyl;

W is $C_nF_{2n+1}$, $C_nF_{2n+1}$, wherein n is 1–3;

A is —$(CH_2)_m$—, —CH=CH—, —$O(CH_2)_n$—, or —$S(CH_2)_n$—;

each $R^7$ independently is hydrogen, $C_1$–$C_6$alkyl, or $(CH_2)_m$ phenyl, wherein m is 0–4; and $R^8$ is hydrogen, $C_1$–$C_6$alkyl, or 2-di($C_1$–$C_6$alkyl)-amino-2-oxoethyl; or a pharmaceutically acceptable salt thereof.

Preferred compounds included within the scope of formula (I) are:

(E)-3-[2-n-butyl-1-{4-carboxyphenyl)methyl}-1H-imidazol-5-yl]-2-(2-thienyl)methyl-2-propenoic acid, (E)-3-[2-n-butyl-1-{4-carboxynaphth-1-yl)methyl}-1H-imidazol-5-yl]-2-(2-thienyl)methyl-2-propenoic acid, (E)-3-[2-n-butyl-1-{2-chloro-4-carboxyphenyl)-methyl}-1H-imidazol-5-yl]-2-(2-thienyl)methyl-2-propenoic acid, and (E)-3-[2-n-butyl-1-{4-carboxy-2,3-dichlorophenyl)-methyl}-1H-imidazol-5-yl]-2-(2-thienyl)methyl-2-propenoic acid; or a pharmaceutically acceptable salt thereof.

Particularly preferred compounds are (E)-3-[2-n-butyl-1-{(4-carboxyphenyl)methyl}-1H-imidazol-5-yl]-2-(2-thienyl)methyl-2-propenoic acid and (E)-3-[2-n-butyl-1-{4-carboxynaphth-1-yl)methyl}-1H-imidazol-5-yl]-2-(2-thienyl)methyl-2-propenoic acid; or a pharmaceutically acceptable salt thereof.

The most preferred compound of this invention is (E)-3-[2-n-butyl-1-{(4-carboxyphenyl)methyl]-1H-imidazolyl-5-yl]-2-(2-thienyl)methyl-2-propenoic acid methanesulfonate.

The compounds of formula (I) are prepared following the methods described in European Patent Publication Number EP 0 403 159, published on Dec. 19, 1990.

Substituted imidazoles, which are described in U.S. application Ser. No. 07/746,024, filed Aug. 14, 1991, are prepared following the methods described in European Publication Number EP 0 403 158, published on Dec. 19, 1990.

Preferred compounds included within the scope of this class of AII receptor antagonists are:

(E)-3-[2-n-butyl-1-{(2-chlorophenyl)methyl}-1H-imidazol-5-yl]-2-(3,4-methylenedioxyphenyl)methyl-2-propenoic acid, (E)-3-[2-n-butyl-1-{(4-carboxyphenyl)methyl)-1H-imidazol-5-yl]-2-n-butyl-2-propenoic acid, and (E)-3-[2-n-butyl-1-{(4-carboxyphenyl)methyl]-1H-imidazol-5-yl]-2-n-benzyl-2-propenoic acid; or a pharmaceutically acceptable salt thereof.

Substituted imidazoles, which are described in U.S. application Ser. No. 07/590,207, filed Sep. 28, 1990, are prepared following the methods described in European Publication Number EP 0 425 211, published on May 2, 1991.

Preferred compounds included within the scope of this class of AII receptor antagonists are:

(E)-1-[2-n-butyl-1-{(4-carboxyphenyl)methyl}-1H-imiidazol-5-yl]-2-(1H-tetrazol-5-yl)-3-(2-thienyl)-1-propene and (E)-1-[2-n-butyl-1-{(4-(1H-tetrazol-5-yl)phenyl)-methyl}-1H-imidazol-5-yl]-2-(1H-tetrazol-5-yl)-3-{2-thienyl)-1-propene; or a pharmaceutically acceptable salt thereof.

Substituted imidazoles, which are described in U.S. Ser. No. 07/590,206 filed, Sep. 28, 1990, are prepared following the methods described in European Publication Number EP 0 427 463, published on May 15, 1991.

Preferred compounds included within the scope of formula (II) are:

N-[{1-(4-carboxyphenyl)methyl]-2-n-butyl-1H-imidazol-5-yl}methyl]-β-(2-thienyl)alanine and N-[{1-(2-chlorophenyl)methyl]-2-n-butyl-1H-imidazol-5-yl}methyl]-β-(2-thienyl)alanine; or a pharmaceutically acceptable salt thereof.

Substituted imidazoles, which are described in U.S. Ser. No. 07/621,491, filed, Nov. 30, 1990, are prepared following the methods described in European Publication Number EP 0 437 103, published Jul. 17, 1991.

Preferred compounds included within the scope of the class or AII receptor antagonist are N-[{2-n-buryl-1-(2-chlorophenyl)methyl-1H-imidazol-5-yl )methylcarbonyl]-L-phenylalanine and N-[{2-n-butyl-1-(2-chorophenyl)methyl-1H-imidazol-5-yl}methylcarbonyl]-L-(2-thienyl)alanine; or a pharmaceutically acceptable salt thereof.

Substitutecd imidazoles of the formula (II);

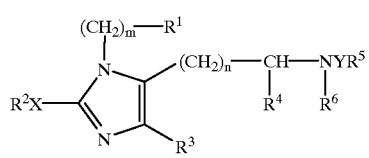

(II)

in which;

$R^1$ is adamantyl, or phenyl, biphenyl, or naphthyl, with each aryl group being unsubstizuted or substituted by one to three substituents selected from Cl, Br, F, I, $C_1$–$C_6$alkyl, nitro, $CO_2R^7$, tetrazol-5-yl, $C_1$–$C_6$alkoxy, hydroxy, $SC_1$–$C_6$alkyl, $SO_2NR^7R^7$, $NHSO_2R^7$, $SO_3H$, $CONR^7R^7$, CN, $SO_2C_1$–$C_6$alkyl, or $C_nF_{2n+1}$;

$R^2$ is $C_2$–$C_{10}$alkyl unsubstituted or substituted by $CO_2H$, OH, or $NR^7R^7$, $C_3$–$C_{10}$alkenyl, $C_3$–$C_{10}$alkynyl, $C_3$–$C_6$cycloalkyl, or $(CH_2)_{0-8}$phenyl unsubstituted or substituted by one to three substituents selected from $C_1$–$C_6$alkyl, nitro, Cl, Br, F, I, hydroxy, $C_1$–$C_6$alkoxy, $NR^7R^7$, $CO_2R^7$, CN, or $CONR^7R^7$, X is a single bond, S, or O;

$R^3$ is hydrogen, Cl, Br, F, I, CHO, hydroxyrmethyl, $COOR^7$, $CONR^7R^7$, $NO_2$, or $C_nF_{2n+1}$;

each n is 1–3;

m is 0–4;

$R^4$ is $CO_2R_7$, $CONR^7R^7$, or tetrazol-5-yl;

Y is a single bond or a carbonyl group;

$R^5$ is hydrogen, $C_1$–$C_8$alkyl, $C_3$–$C_6$cycloalkyl, $(CH_2)_{0-4}$phenyl, or $(CH_2)_{0-3}$CH-diphenyl wherein each phenyl group independently is unsubstituted or substituted by one to three substituents selected from $C_1C_6$ alkyl, nitro, Cl, Br, F, I, hydroxy, $C_1$–$C_6$alkyl, $NR^7R^7$, $CO_2R^7$, or $CONR^7R^7$;

$R^6$ is hydrogen or $C_{1-6}$alkyl; and each $R_7$ independently is hydrogen, $C_1$–$C_4$alkyl, or $(CH_2)_{0-4}$phenyl; or a pharmaceutically acceptable salt thereof.

Preferred compounds included within the scope of formula (VI) are 3-[(2-chlorophenyl)methyl]-2-propylthio-N-butrylhistidine and 3-[(2-chlorophenyl)methyl]-2-n-butyl-N-butyrylhistidine; or a pharmaceutically acceptable salt thereof.

Compounds of formula (II) are prepared as illustrated by Example 1.

Substituted imidazoles of the formula (III):

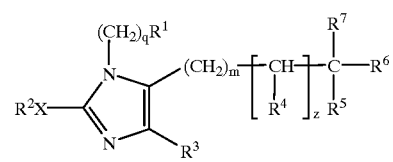

(III)

in which:

$R^1$ is adamanthylmethyl, or phenyl, biphenyl, or naphthyl, with each aryl group being unsubstituted or substituted by one to three substituents selected from Cl, Br, F, I, $C_{1-6}$alkyl, nitro, $CO_2R^8$, tetrazol-5-yl, $C_{1-6}$alkoxy, hydroxy, $SC_{1-4}$alkyl, $SO_2NHR^8$, $NHSO_2R^8$, $SO_3H$, $CONR^8R^8$, CN, $SO_2C_{1-4}$alkyl, or $C_nF_{2n+1}$, wherein n is 1–3;

$R^2$ is $C_{2-10}$alkyl, $C_{3-10}$alkenyl, $C_{3-10}$alkynyl, $C_{3-6}$cycloalkyl, or $(CH_2)_{0-8}$phenyl unsubstituted or substituted by one to three substituents selected from $C_{1-6}$alkyl, nitro, Cl, Br, F, I, hydroxy, $C_{1-6}$alkoxy, $NR^8R^8$, $CO_2R^8$, CN, or $CONR^8R^8$;

X is a single bond, S, or O;

$R^3$ is hydrogen, Cl, Br, F, I, CHO, hydroxymethyl, $CO_2R^8$, $NO_2$, or $C_nF_{2n+1}$ wherein n is 1–3;

q is 0 to 4;

m is 0 to 2;

$R^4$ is H or $C_{1-6}$alkyl;

z is 0 to 1;

$R^5$ is $C_{3-6}$alkyl, $C_{3-6}$alkenyl, phenyl-Y-, 2- or 3-thienyl-Y-, 2- or 3-furyl-Y-, 2-, 3-, or 4-pyridyl-Y-, tetrazolyl-Y-, triazolyl-Y-, imidazolyl-Y-, pyrazolyl-Y-, thiazolyl-Y-, pyrrolyl-Y-, or oxazolyl-Y-, with each aryl ring being unsubstituted or substituted by $C_{1-6}$alkyl, Cl, Br, F, I, $C_{1-6}$alkoxy, $NR^8R^8$, $CO_2R^8$, or $CONR^8R^8$;

Y is a single bond or $C_{1-6}$alkyl which is branched or unbranched;

$R^6$ is $CO_2R^8$, $CONR^8R^8$, or tetrazol-5-yl;

$R^7$ is H, $CO_2R^8$, or $C_{1-6}$alkyl; and each $R^8$ independently is hydrogen, $C_{1-6}$alkyl, or $(CH_3)_{0-4}$ phenyl; or a pharmaceutically acceptable salt thereof.

A preferred compound included within the scope of formula (VII) is 3-[2-n-butyl-1-{(2-chlorophenyl)methyl}-1H-imidazol-5-yl]-2-benzylpropanoic acid or a pharmaceutically acceptable salt thereof.

Compounds of formula (III) are prepared as illustrated by Example 2.

Substituted imidazoles of the formula (IV) which are described in U.S. application Ser. No. 07/621,188, filed Nov. 30, 1990:

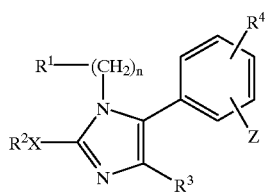

(IV)

in which:

$R^1$ is adamantylmethyl, or phenyl, biphenyl, or naphthyl, with each aryl group being unsubstituted or substituted by one to three substituents selected from Cl, Br, F, I, $C_1$–$C_6$alkyl, nitro, $CO_2R^5$, $C_1$–$C_6$alkoxy, hydroxy, $SC_1$–$C_6$alkyl, $SO_2C_1$–$C_6$alkyl, tetrazol-5-yl, $SO_2NHR^5$, $NHSO_2R^5$, $SO_3H$, $PO(OR^5)_2$, $CONR^5R^5$, CN, $NR^5R^5$, $NR^5COH$, $NR^5COC_1$–$C_6$alkyl, $NR^5CON(R^5)_2$, $NR^5COW$, $SO_2W$, or W;

$R^2$ is $C_2$–$C_{10}$alkyl, $C_3$–$C_{10}$alkenyl, $(CH_2)_{0-8}$-$C_{3-6}$ cycloalkyl, or $(CH_2)_{0-8}$phenyl unsubstituted or substituted by one to three substituents selected from $C_1$–$C_6$alkyl, nitro, Cl, Br, F, I, hydroxy, $C_1$–$C_6$alkoxy, tetrazol-5-yl, $NR^5R^5$, $CO_2R^5$, CN, $CONR^5R^5$, W, $NR^5COH$, $NR^5COC_1$–$C_6$-alkyl, $NR^5COW$, $SO_2W$, $SO_2C_1$–$C_6$alkyl, or $SC_1$–$C_6$alkyl;

X is a single bond, S, $NR^5$, or O;

n is 0–4;

$R^3$ is hydrogen, Cl, Br, F, I, CHO, hydroxymethyl, $C_1$–$C_6$alkyl, $NR^5R^5$, $CO_2R^5$ $CONR^5R^5$, $NO_2$, CN, phenyl, or W;

$R^4$ is $CO_2R^5$, $CONR^5R^5$, or tetrazol-5-yl;

Z is hydrogen, Cl, Br, F, I, $C_1$–$C_6$alkyl, $C_1$–$C_6$alkoxy, hydroxy, CN, $NO_2$, $CO_2R^5$, $COR^5R^5$, W, phenyl-Y-, naphthyl-Y-, thienyl-Y-, furyl-Y-, pyrazolyl-Y-, imidazolyl-Y-, thiazolyl-Y-, tetrazolyl-Y-, pyrrolyl-Y-, triazolyl-Y-, oxazolyl-Y-, or isoxazolyl-Y-, with each aryl or heteroaryl group being unsubstituted or substituted by $C_1$–$C_6$alkyl, $C_1$–$C_6$alkoxy, Cl, Br, F, I, $CO_2R^5$, hydroxy, $NO_2$, CN, $CONR^5R^5$, or W;

Y is a single bond or $C_1$–$C_6$alkyl, which is straight or branched;

W is $C_mF_{2m+1}$, wherein m is 1–4,; and each $R^5$ independently is H or $C_1$–$C_6$alkyl; or a pharmaceutically acceptable salt thereof.

A preferred compound included within the scope of formula (IV) is 3-[2-n-butyl-1-{(2-chlorophenyl)methyl}-1H-imidazol-5-yl]benzoic acid or a pharmaceutically acceptable salt thereof.

Compounds of formula (IV) are prepared as illustrated by Example 3.

Substituted benzimidazoles of the formula (V):

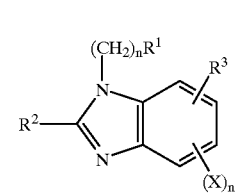

(V)

in which:

$R^1$ is —C(O)NH—CH(Y)—$(CH_2)_n$-aryl, —C(O)NH—CH(Y)—$(CH_2)_n$-heteroaryl, or phenyl unsubstituted or substituted by one to three substituents selected from Cl, Br, F, I, $C_{1-6}$alkyl, $C_{1-6}$alkoxy, OH, CN, $NO_2$, $CO_2R^4$, tetrazol-5-yl, $CONR^4R^4$, $SO_3H$, $C_mF_{2m+1}$, $SC_{1-6}$alkyl, or $SO_2C_{1-6}$alkyl;

$R^2$ is hydrogen, $C_{2-10}$ alkyl, $C_{3-10}$alkenyl, $C_{3-6}$-cycloalkyl, $C_mF_{2m+1}$, or $(CH_2)_{0-8}$phenyl unsubstituted or substituted by one to three substituents selected from $C_{1-6}$alkyl, $C_{1-6}$alkoxy, Cl, Br, F, I, OH, $NO_2$, $C_mF_{2m+1}$, $CO_2R^4$, or $NR^4R^4$;

$R^3$ is —$(CH_2)_n$-Y, —CH=CY—$(CH_2)_n$-aryl, —CH=CY—$(CH_2)_n$-heteroaryl, —$(CH_2)_n$ —C(O)—NH—CH(Y)—$(CH_2)_n$-aryl —$(CH_2)_n$ —C(O)—NH—CH(Y) —$(CH_2)_n$heteroaryl, —$(CH_2)_m$—NH—CH(Y)—$(CH_2)_n$-aryl or —$(CH_2)_m$—NH—CH(Y) —$(CH_2)_n$-heteroaryl, when $R^1$ is an optionally substituted phenyl group; or H when $R^1$ is —C(O)NH—CH(Y)—$(CH_2)_n$-aryl or —C(O)NH—CH(Y)—$(CH_2)_n$-heteroaryl;

Y is $CO_2R^4$ or tetrazol-5-yl;

X is Cl, Br, F, I, $C_mF_{2m+1}$, $C_{1-6}$alkyl, $C_{1-6}$alkoxy, OH, O-phenyl, $CO_2R^4$, tetrazol-5-yl, CN, or $(CH_2)_{0-4}$phenyl unsubstituted or substituted by Cl, Br, F, I, $C_{1-6}$alkyl, $C_{1-6}$alkoxy, OH, $C_mF_{2m+1}$, CN, $CO_2R^4$, $NO_2$, or $NR^4R^4$;

aryl is phenyl, biphenyl, or naphthyl wherein each aryl group is unsubstituted or substituted by $C_{1-6}$alkyl, $C_{1-6}$alkoxy, Cl, Br, F, I, OH, $NO_2$, $CF_3$, $CO_2R^4$, or $NR^4R^4$;

heteroaryl is 2- or 3-thienyl, 2-, or 3-furanyl, 2-, 3-, or 4-pyridyl, pyrimidyl, imidazolyl, thiazolyl, triazolyl, or tetrazolyl wherein each heteroaryl group is unsubstituted or substituted by $C_{1-6}$alkyl, $C_{1-6}$alkoxy, Cl, Br, F, I, OH, $NO_2$, $CF_3$, $CO_2R^4$, or $NR^4R^4$;

each m independently is 1–3;

each n independently is 0–2; and each $R^4$ independently is H or $C_{1-6}$alkyl; or a pharmaceutically acceptable salt thereof.

A preferred compound included within the scope of formula (V) is 2-n-butyl-1-(4-carboxyphenyl)methyl-5-chloro-1H-benzimidazole-7-carboxylic acid or a pharmaceutically acceptable salt thereof.

Compounds of formula (V) are prepared following the methods described in Patent Cooperation Treaty Publication Number WO 91/16313, published Oct. 31, 1991. Formula (V) compounds are prepared as illustrated by Example 4.

The above descriptions on pages 2–11 of classes of AII receptor antagonists for use in the present invention were taken from the noted patent applications and publications. Reference should be made to such patent applications and publications for their full disclosure, the entire disclosure of each of which is incorporated herein by reference.

The following angiotensin II receptor antagonists are also included within the scope of the instant invention. Since it is contemplated that any AII receptor antagonist will possess the novel utility herein described, the list below does not limit the scope of the present invention.

| AII Analog* | Reference Citing AII Receptor Blocking Activity |
|---|---|
| $Sar^1$ $Ala^8$ | Clin. Sci. 57: 71, 1979 |
| $Sar^1$ $Ile^8$ | Endocrinology 107(5): 1365, 1980 |
| $Succ^1$ $Val^5$ $Phenylgly^8$ | Clin. Sci. Mol. Med. 51: 4305, 1976 |
| $desAsp^1$ $Ile^8$ | Am. J. Physiol. 236(3): F252, 1976 |
| $Sar^1$ $Thr^8$ | Clin. Sci. Mol. Med. 51: 3855, 1976 |
| $Sar^1$ $Cys\text{-}Me^8$ | J. Cardiovasc. Pharm. 5: 1025, 1983 |
| $Sar^1$ $Tyr\text{-}Me^4$ | Life Sci. 34: 317, 1983 |
| $Gly^8$ | Can J. Physiol Pharm. 57: 121, 1979 |
| $Ile^8$ | Can J. Physiol Pharm. 57: 121, 1979 |
| $Leu^8$ | Can J. Physiol Pharm. 57: 121, 1979 |
| $Sar^1$ $Leu^8$ | Can J. Physiol Pharm. 57: 121, 1979 |
| $desAsp^1$ $Leu^8$ | Can J. Physiol Pharm. 57: 121, 1979 |
| $Sar^1$ $Me\text{-}Ala^7$ $Ile^8$ | Can J. Physiol Pharm. 57: 763, 1979 |
| $Sar^1$ $DL\text{-}Nipecotamide^7$ $Ile^8$ | Can J. Physiol Pharm. 57: 763, 1979 |
| $Sar^1$ $Sar^7$ $Ile^8$ | Can J. Physiol Pharm. 57: 763, 1979 |
| 8-L-Ala | J. Pharm. Pharmacol. 32: 232, 1980 |
| $Met^8$ | J. Med. Chem. 22(9): 1147, 1979 |
| $Thr^8$ | J. Med. Chem. 22(9): 1147, 1979 |
| $O\text{—}Me\ Thr^8$ | J. Med. Chem. 22(9): 1147, 1979 |
| $N\text{—}Me\ Ile^8$ | J. Med. Chem. 22(9): 1147, 1979 |
| $N\text{—}Me\ Phe^8$ | J. Med. Chem. 22(9): 1147, 1979 |
| $Sar^1$ $Sar^7$ $Leu^8$ | J. Med. Chem. 22(9): 1147, 1979 |
| $Sar^1$ $Sar^7$ $Thr(Me)^R$ | J. Med. Chem. 22(9): 1147, 1979 |
| $Sar^1$ $Sar^7$ $DLaIle^8$ | J. Med. Chem. 22(9): 1147, 1979 |
| $MeIle^1$ $Thr^8$ | J. Med. Chem. 20(2): 253, 1977 |
| $Me_2Gly^1$ $Thr^8$ | J. Med. Chem. 20(2): 253, 1977 |
| $GdnAC^1$ $Thr^8$ | J. Med. Chem. 20(2): 253, 1977 |
| $desAsp^1$ $Thr^8$ | J. Med. Chem. 20(2): 253, 1977 |
| $Sar^1$ $Ser(Me)^8$ | J. Med. Chem. 20(2): 253, 1977 |
| $Sar^1$ $Thr^8$ | J. Med. Chem. 20(2): 253, 1977 |
| $Sar^1$ $Thr(Me)^8$ | J. Med. Chem. 19(2): 244, 1976 |
| $MeAspNH_2^1$ $Ile^8$ | J. Med. Chem. 19(2): 244, 1976 |
| $Sar^1$ $MeTyr^4$ $Ile^8$ | J. Med. Chem. 19(2): 244, 1976 |
| $Sar^1$ $MeIle^5$ $Ile^8$ | J. Med. Chem. 19(2): 244, 1976 |
| $Sar^1$ $MeIle^8$ | J. Med. Chem. 19(2): 244, 1976 |
| $Sar^1$ $MeIle^5$ $MeIle^8$ | J. Med. Chem. 19(2): 244, 1976 |
| $Sar^1$ $Thr\ (O\text{—}/\text{—}Me)^8$ | J. Med. Chem. 19(2): 244, 1976 |
| $Sar^1$ $Met^8$ | J. Med. Chem. 19(2): 244, 1976 |
| $Sar^1$ $Ser^8$ | J. Med. Chem. 19(2): 244, 1976 |
| $Ile^5$ $Ala^8$ | J. Med. Chem. 13: 181, 1970 |
| $Ile^5$,8-(3-amino-4-phenyl)butyric acid | J. Med. Chem. 13: 181, 1970 |
| $Asn^1$ $Ala^8$ | Circ. Res. 29: 664, 1971 |
| $Sar^1$ $Cys(Me)^8$ | Circ. Res. 46: 720, 1980 |
| $Phe^4$ $Tyr^8$ | Proc. Nat Acad. Sci. 67: 1624, 1970 |
| $OctanoylLeu^8$ | J. Med. Chem. 20: 898, 1977 |
| $Cys^8$ | Cir. Res. 31: 862, 1972 |
| $Phe^4$ $Tyr^8$ | Cir. Res. 31: 862, 1972 |
| $desAsp^1$ $Phe^4$ $Tyr^8$ | Cir. Res. 31: 862, 1972 |
| $para\text{-}fluoroPhe^4$ | Cir. Res. 31: 862, 1972 |
| $para\text{-}fluoroPhe^8$ | Cir. Res. 31: 862, 1972 |

*Abbreviations indicate substitutions in the Angiotensin II sequence Asp-Arg-Val-Tyr-Ile-His-Pro-Phe with the location of the substitution identified by the superscript.

Other classes of AII receptor antagonists are disclosed in the following:

Sipos et al., U.S. Pat. No. 3,751,404, issued Aug. 7, 1973. A particularly preferred compound in this class of AII receptor antagonists is Sar-Arg-Val-Tyr-Val-His-Pro-β-Ala-OH which is also referred to as Saralasin.

Regoli et al., U.S. Pat. No. 3,907,762, issued Sep. 23, 1975. Examples of suitable compounds within this class are Asp-Arg-Val-Tyr-Ile-His-Pro-Val-OH and Asp-Arg-Val-Tyr-Ile-His-Pro-α-amino-n-butyric acid.

Nyeki et al., U.S. Pat. No. 4,388,304, issued Jun. 14, 1983. Compounds disclosed in this patent include Sar-Arg-Val-Tyr-Ile-His-Pro-Ile-methyl ester and hydroxyacetyl-Arg-Val-Tyr-Ile-His-Pro-Thr-methyl ester. The same or similar compounds are also disclosed in European Patent No. 34,259.

Sipos et al., U.S. Pat. No. 3,886,134 issued May 27, 1975. Examples of compounds of this class are Sar-Arg-Val-Tyr-Val-His-Pro-Ala-OH, Ser-Arg-Val-Tyr-Val-His-Pro-Ala-OH, and Asn-Arg-Val-Tyr-Val-His-Pro-D-Leu-OH.

Kisfaludy et al., U.S. Pat. No. 4,179,433, issued Dec. 18, 1979. Examples of this class of compounds include aminooxyacetyl-Arg-Val-Tyr-Ile-His-Pro-Leu-OH and D-α-aminooxypropionyl-Arg-Val-Tyr-Ile-His-Pro-Leu-OH.

Hallinan et al., U.S. Pat. No. 4,204,991, issued May 27, 1980. See also West German Offenlegungschrift No. 2846200 (Chemical Abstracts, Vol. 91, Abstract No. 74989d).

Kisfaludy et al., U.S. Pat. No. 4,209,442, issued Jun. 24, 1980. Examples include hydroxyacetyl-Arg-Val-Tyr-Ile-His-Pro-Leu-OH, hydroxyacetyl-Arg-Val-Tyr-Ile-His-Pro-Ala-OH, and α-hydroxypropionyl-Arg-Val-Tyr-Ile-His-Pro-Ile-OH.

Nyeki et al., U.S. Pat. No. 4,330,532, issued May 18, 1982. Exemplary compounds of this class are Sar-Arg-Val-Tyr-Ile-His-Pro-Lac, Sar-Arg-Val-Tyr-Ile-His-Pro-Lac ($OC_2H_5$), and Sar-Arg-Val-Tyr-Ile-His-Pro-2-hydroxy-3-methylvaleric acid.

Furukawa et al., U.S. Pat. No. 4,340,598 issued Jun. 20, 1982. Examples include 1-benzyl-4-chloro-2-phenylimidazole-5-acetamide, 1-benzyl-2-n-butyl-4-chloroimidazole-5-acetamide, and 1-benzyl-2-n-butyl-5-chloroimadazole-4-acetic acid.

Furukawa et al., U.S. Pat. No. 4,355,040, issued Oct. 19, 1982. Examples include 1-(2-chlorobenzyl)-2-n-butyl-4-chloroimidazole-5-acetic acid and 1-benzyl-4-chloro-2-(4-chloro-3,5-dinitrophenyl)imidazole-5-acetic acid.

Furukawa, et al., in European Patent Publication No. 103 647, published Mar. 28, 1984. A preferred compound included within the scope of this class of AII receptor antagonists is 4-chloro-1-(4-hydroxy-3-methylbenzyl)-2-phenylimidazole-5-acetic acid or a pharmaceutically acceptable salt thereof.

Carini et al., in European Patent Publication No. 253 310, published Jan. 20, 1988 and U.S. application Ser. No. 50341 filed May 22, 1987. Preferred compounds included within this class of AII receptor antagonists are 2-n-butyl-4-chloro-1-[(2'-(1H-tetrazol- 5-yl)biphenyl-4-yl)methyl]-5-(hydroxymethyl)imidazole and 2-n-butyl-4-chloro-1-[(2'-(carboxybiphenyl-4-yl)methyl]-5-(hydroxymethyl)-imidazole; or a pharmaceutically acceptable salt thereof.

Blankley et al., in European Patent Publication No. 245 637, published Nov. 19, 1987 and U.S. application Ser. No. 847067, filed Apr. 1, 1986. Preferred compounds included within the scope of this class of AII receptor antagonists are 1-(2-phenylethyl)-5-phenylacetyl-4,5,6,7-tetrahydro-1H-imidazo[4,5-c]pyridine-6-carboxylic acid and 1-(4-amino-3-methylphenyl)methyl-5-diphenylacetyl-4,5,6,7-tetrahydro-1H-imidazo[4,5-c]pyridine-6-carboxylic acid; or a pharmaceutically acceptable salt thereof.

Carini et al., in European Patent Publication No. 323 841, published Jul. 12, 1989 and U.S. application Ser. No. 07/279,193, filed Dec. 6, 1988. Preferred compounds included in this class of AII receptor antagonists are 5-n-propyl-1-[(2'-carboxybiphenyl-4-yl)methyl]pyrrole-2-carboxylic acid, 3-methoxymethyl-5-n-propyl-4-[(2'-(1H-tetrazol-5-yl)biphenyl-4-yl)methyl]-1,2,4-triazole, and 3-methoxymethyl-5-n-butyl-1-[2'-carboxybiphenyl-4-yl)methyl]pyrazole; or a pharmaceutically acceptable salt thereof.

Carini, et al., U.S. Pat. No. 4,880,804, issued Nov. 14, 1989. Preferred compounds included within this class of AII receptor antagonists are 2-n-butyl-1-[(2'-carboxybiphenyl-4-yl)methyl]-5-hydroxymethylbenz-imidazole and 2-n-butyl-1-[(2'-carboxybiphenyl-4-yl)methyl]-6-hydroxymethylbenzimidazole; or a pharmaceutically acceptable salt thereof.

Carini, et al., U.S. Pat. No. 4,916,129, issued Apr. 10, 1990. A preferred compound included within this class of AII receptor antagonists is 5-[4-(3-(N-iso-propylamino) hydroxypropoxy)indole-2-carboxamidomethyl]-2-n-butyl-1-[(2'-carboxybiphenyl-4-yl)methyl]-4-chloroimidazole or a pharmaceutically acceptable salt thereof.

Rosenberg, et al., U.S. Pat. No. 4,857,507, issued Aug. 15, 1989. Examples include Boc-Phe-Leu amide of (4S)-3-oxo-4-amino-2,2-difluoro-1-isopropyl-mercapto-5-cyclohexylpentane and Boc-Phe-Leu amide of (3R, 4S, EZ)-3-hydroxy-4-amino-2-fluoro-1-isopropyl-sulfonyl-5-cyclohexyl-1-pentene; or a pharmaceutically acceptable salt thereof.

Wissmann et al. U.S. Pat. No. 4,013,791, issued Mar. 22, 1977. An example of such compounds is succinamoyl-Arg-Val-Tyr-Val-His-Pro-Phegly-OH where Phegly-OH is a L-C-phenylglycine residue.

Bumpus et al., U.S. Pat. No. 3,923,769, issued Dec. 2, 1975.

Bumpus et al., U.S. Pat. No. 3,923,770, issued Dec. 2, 1975.

Bumpus et al. U.S. Pat. No. 3,923,771, issued Dec. 2, 1975.

Bumpus et al., U.S. Pat. No. 3,925,345, issued Dec. 9, 1975.

Bumpus et al., U.S. Pat. No. 3,976,770, issued Aug. 24, 1976.

Wille U.S. Pat. No. 3,915,948, issued Oct. 28, 1975. An example of an AII receptor antagonist included in this reference is Sar-Arg- Val-Tyr-Val-His-Pro-OH Lifer, et al., European Patent Publication Number EP 0 438 869, published Jul. 31, 1991 and U.S. application Ser. No. 07/444,456, filed Nov. 30, 1989. A preferred compound of this class of AII receptor antagonists is α-hexyl-4-[(2-carboxy-3-hydroxybenzoyl)amino]-1H-imidazole-1-acetic acid ethyl ester or a pharmaceutically acceptable salt or solvate thereof.

Chakravarty, et al., European Patent Publication Number EP 0 401 030, published Dec. 5, 1990 and U.S. application Ser. No. 07/522,662, filed May 16, 1990. A preferred embodiment of this class of AII receptor antagonists includes 2-n-butyl-3-(2'-tetrazol-5-yl)biphenyl-4-yl) methyl06,7-dihydroimidazo[4,5-e][1,4]diazepine-8(3H)-one or a pharmaceutically acceptable salt thereof.

Chakravarty, et al., European Patent Publication Number EP 0 400 974, published Dec. 5, 1990 and U.S. application Ser. No. 07/516,286, filed May 4, 1990. An example included within the scope of this class of AII receptor antagonists is 5,7-dimethyl-2-ethyl-3-(2'-(tetrazol-5-yl) biphenyl-4-yl)methyl-3H-imidazo[4,5-b]pyridine or a pharmaceutically acceptable salt thereof.

Chakravarty, et al., European Patent Publication Number EP 0 400 835, published Dec. 5, 1990 and U.S. application Ser. No. 07/504,441, filed Apr. 4, 1990. A preferred embodiment of this class of AII receptor antagonists includes 4,6-dimethyl-2-ethyl-1-[2-(tetrazol-5-yl)biphenyl-4-yl] methylbenzimidazole or a pharmaceutically acceptable salt thereof.

Ashton, et al., European Patent Publication Number EP 0 409 332, published Jan. 23, 1991 and U.S. application Ser. No. 07/503,352, filed Apr. 2, 1990. A preferred embodiment of this class of AII receptor antagonists includes 3-n-butyl-4-[4-(2-carboxy-benzamido)benyl]-5-(2-methylbenzylthio)-4-1,2,4-triazole or a pharmaceutically acceptable salt thereof.

Greenlee, et al., European Patent Publication Number EP 0 407 102, published Jan. 9, 1991 and U.S. application Ser. No. 07/516,502, filed Apr. 25, 1990. A preferred embodiment of this class of AII receptor antagonists includes 2-n-butyl-1,5-dihydro-4,5-dimethyl-1-[(2'-{1H-tetrazol-5-yl}{(1,1-biphenyl}-4-yl)methyl]-pyrrolo[pyrrolo[3,4-d] imidazole or a pharmaceutically acceptable salt thereof.

Carini, et al., European Patent Publication Number EP 0 324 377, published Jul. 19, 1989 and U.S. application Ser. No. 07/279,194, filed Dec. 6, 1988. A preferred embodiment of this class of AII receptor antagonists includes 2-n-propyl-4-pentafluoroethyl-1-[2'-(1H-tetrazol-5-yl)biphenyl-4-yl) methyl]imidazole-5-carboxylic acid or a pharmaceutically acceptable salt thereof.

Oku, et al., European Patent Publication Number EP 0 3426 021, published May 8, 1991. A preferred embodiment of this class of AII receptor antagonists includes 2-n-butyl-7-methyl-3-[(2-(1H-tetrazol-5-yl)biphenyl-4-yl]methyl]-3H-imidazo[4,5-b]pyridine or a pharmaceutically acceptable salt thereof.

Roberts, et al., European Patent Publication Number EP 0 412 848, published Feb. 13, 1991. A preferred embodiment of this class of AII receptor antagonists includes 2-methyl-4-(2'-(1H-tetrazol-5-yl)biphenyl-4-yl)methoxy]quinoline or a pharmaceutically acceptable salt thereof.

Roberts, et al., Patent Cooperation Treaty Application Publication Number WO 91/07404, published May 30, 1991. A preferred embodiment of this class of AII receptor antagonists includes 2-ethyl-4-[(2'-(1H-tetrazol-5-yl) biphenyl-4-yl)methoxy-1,5-naphthyridine or a pharmaceutically acceptable salt thereof.

Roberts, et al., European Patent Publication Number EP 0 399 732, published Nov. 28, 1990. A preferred embodiment of this class of AII receptor antagonists includes 4-[(2-n-butyl-1H-benzimidazol-1-yl)methyl-N-phenylsulphonlybenzamide or a pharmaceutically acceptable salt thereof.

Miyake, et al., European Patent Publication Number EP 0 420 237, published Mar. 3, 1991. A preferred embodiment of this class of AII receptor antagonists includes 7-methyl-2-n-propyl-3-[(2"(1H-tetrazol-5-yl)biphenyl-4-yl)methyl]-3H-imidazo[4,5-b] or a pharmaceutically acceptable salt thereof.

Narr, et al., European Patent Publication Number EP 0 392 317, published Nov. 17, 1990. A preferred embodiment of this class of AII receptor antagonists includes 4'-[(6-n-butanoylamino-2-n-butyl-benzimidazol-1-yl)methyl] biphenyl-2-carboxylic acid or a pharmaceutically acceptable salt thereof.

An angiotensin II receptor antagonist of the formula (VI):

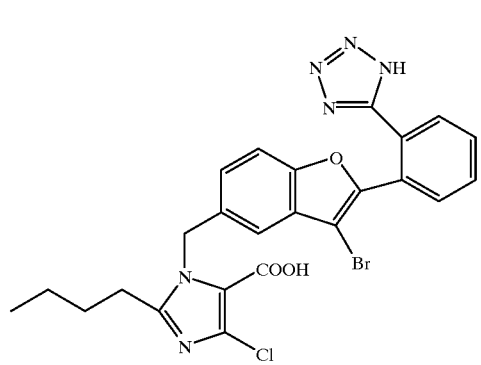

(VI)

which is 2-n-butyl-4-chloro-1-{[3-bromo-2-[2-(tetrazol-5-yl)phenyl]benzofuranyl-4-yl]methyl}imidazole-5-acetic acid or a pharmaceutically acceptable salt thereof.

The above descriptions of classes of AII antagonists for use in the present invention were taken from pending patent applications, noted patents, and publications or from abstracts thereof. Reference should be made to such patents and publications themselves for their full disclosures of such classes and specific compounds within such classes, the entire disclosure of such patents and publications being incorporated herein by reference. Furthermore, examples 1–4 teach how to make compounds encompassed by the generic Formulae of (II)–(V).

Many AII antagonists are known in the art and may be prepared by known methods or by variations thereof. Certain AII antagonists employed in the invention may exist in isomeric form. This invention includes all such isomers both in pure form and admixture, including racemic mixtures and their pharmaceutically acceptable salts.

Angiotensin II antagonist activity is assessed by in vitro methods. In vitro antagonist activity is determined by the ability of the compounds to compete with $^{125}$I-angiotensin II for binding to vascular angiotensin II receptors and by their ability to antagonize the contractile response to angiotensin II in the isolated rabbit aorta. For the purposes of the present invention the preferred AII antagonists are compounds which are capable of inhibiting the action of AII by at least 50% at a concentration of 1 mM or less, and especially preferred AII antagonists are compounds which are capable of inhibiting the action of AII by at least 50% at a concentration of 25 nM or less when tested by the following standard methods.

Binding

The radioligand binding assay is a modification of a method previously described in detail (Gunther et al., *Circ. Res.* 47:278, 1980). A particular fraction from rat mesenteric arteries is incubated in Tris buffer with 80 pM of $^{125}$I-angiotensin II with or without angiotensin II antagonists for 1 hour at 25° C. The incubation is terminated by rapid filtration and receptor bound $^{125}$I-angiotensin II trapped on the filter is quantitated with a gamma counter. The potency of angiotensin II antagonists is expressed as the $IC_{50}$ which is the concentration of antagonist needed to displace 50% of the total specifically bound angiotensin II.

Aorta

The ability of the compounds to antagonize angiotensin II induced vasoconstriction is examined in the rabbit aorta. Ring segments are cut from the rabbit thoracic aorta and suspended in organ baths containing physiological salt solution. The ring segments are mounted over metal supports and attached to force displacement transducers which are connected to a recorder. Cumulative concentration response curves to angiotensin II are performed in the absence of antagonist or following a 30-minute incubation with antagonist. Antagonist dissociation constants ($K_B$) are calculated by the dose ratio method using the mean effective concentrations.

In the therapeutic use for the treatment of diabetic nephropathy the AII receptor antagonizing compounds of this invention are incorporated into standard pharmaceutical compositions. They can be administered orally, parenterally, rectally, topically or transdermally.

The compounds of the instant invention and their pharmaceutically acceptable salts which are active when given orally can be formulated as liquids, for example syrups, suspensions or emulsions, tablets, capsules and lozenges.

A liquid formulation will generally consist of a suspension or solution of the compound or pharmaceutically acceptable salt in a suitable liquid carrier(s) for example, ethanol, glycerine, non-aqueous solvent, for example, polyethylene glycol, oils, or water with a suspending agent, preservative, flavouring or colouring agent.

A composition in the form of a tablet can be prepared using any suitable pharmaceutical carrier(s) routinely used for preparing solid formulations. Examples of such carriers include magnesium stearate, starch, lactose, sucrose and cellulose.

A composition in the form of a capsule can be prepared using routine encapsulation procedures. For example, pellets containing the active ingredient can be prepared using standard carriers and then filled into a hard gelatin capsule; alternatively, a dispersion or suspension can be prepared using any suitable pharmaceutical carrier(s), for example aqueious gums, celluloses, silicates or oils and the dispersion or suspension then filled into a soft gelatin capsule.

The compounds of the instant invention and their pharmaceutically acceptable salts which are active when administered parenterally (i.e. by injection of infusion) can be formulated as solutions or suspensions.

A composition for parenteral administration will generally consist of a solution or suspension of the active ingredient in a sterile aqueous carrier or parenterally acceptable oil, for example polyethylene glycol, polyvinyl pyrrolidone, lecithin, arachis oil or sesame oil. Alternatively, the solution can be lyophilised and then reconstituted with a suitable solvent just prior to administration.

A typical suppository composition comprises a compound of the instant invention or a pharmaceutically acceptable salt thereof which is active when administered in this way, with a binding and/or lubricating agent such as polymeric glycols, gelatins or coca butter or other low melting vegetable or synthetic waxes or fats.

A typical transdermal formulation comprises a conventional aqueous or non-aqueous vehicle, for example, a cream, ointment lotion or paste or in the form of a medicated plaster, patch or membrane.

For topical administration, the pharmaceutical compositions adapted include solutions, suspensions, ointments, and solid inserts. Typical pharmaceutically acceptable carriers are, for example, water, mixtures of water and water-miscible solvents such as lower alkanols or vegetable oils, and water soluble ophthalmologically acceptable non-toxic polymers, for example, cellulose derivatives such as methyl cellulose. The pharmaceutical preparation may also contain non-toxic auxiliary substances such as emulsifying, preserving, wetting, and bodying agents, as for example, polyethylene glycols; antibacterial components such as quaternary ammonium compounds; buffering ingredients such as alkali metal chloride; antioxidants such as sodium metabisulfite; and other conventional ingredients such as sorbitan monolaurate.

Preferably the composition is in unit dose form. Doses of the compounds of the instant invention in a pharmaceutical dosage unit will be an efficacious, non-toxic quantity selected from the range of 0.01–200 mg/kg of active compound, preferably 0.1–100 mg/kg. The selected dose is administered to a human patient in need of treatment of diabetic nephropathy induced by angiotensin II from 1–6 times daily, orally, rectally, topically, by injection, or continuously by infusion. Oral dosage units for human administration preferably contain from 10 to 500 mg of active compound. Lower dosages are used generally for parenteral administration. Oral administration is used when safe, effective, and convenient for the patient.

No unacceptable toxicological effects are expected when compounds of the invention are administered in accordance with the present invention.

The following examples are intended to illustrate, but not to limit, the present invention. Examples 1–4 describe how to make certain compounds encompassed by the generic formulae of (II)–(V). The remaining examples are directed to pharmaceutical compositions of this invention. The compounds included in these disclosed compositions are representative of the AII receptor antagonists included within the scope of the instant invention, but therapeutically effective amounts of other AII antagonists as discussed hereinabove may be substituted.

The procedures of Examples 1–4 are illustrative of the synthesis of compounds encompassed by generic formulae (II)–(V). Substitution of starting materials by the appropriate known reagents yields additional compounds within the scope of formulae (II)–(V). Reagents, protecting groups, and functionality on the imidazole and other fragments of the molecule must be consistent with the proposed chemical transformations.

The procedure of Example 1 is illustrative of the synthesis of compounds encompassed by generic formula (II).

EXAMPLE 1

3-[(2-Chlorophenyl)methyl]-2-propylthio-N-butyrylhistidine (i) 5-carboxymethyl-1-(2-chlorophenyl)methyl-2-thio-1H-imidazole A solution of 2-chlorobenzylamine (14.2 g, 0.1 mol) and triethylamine (13.9 mL, 0.1 mol) in dimethylformamide (100 mL) was treated with methyl chloroacetate (10.9 g, 0.1 mol). The mixture was heated at 50° C. for 3.5 hours. The cooled reaction mixture was diluted with diethyl ether, the solids filtered and the concentrated filtrate was flash chromatographed over silica gel with 6:4 hexane in ethyl acetate to provide 15.3 g (71%) of homogenous methyl 2-(N-(2-chloro-phenyl)methyl]amino-acetate. This product (15.2 g, 0.071 mol) in xylene (100 mL) was treated with 98% formic acid (2.74 mL, 0.0711 mol) and the mixture was refluxed for 2.5 hours with a Dean-Stark water separator. Evaporation gave 17.1 g (99%) of methyl 2-[N-(2-chlorophenyl)methyl-N-formyl) aminoacetate. This formylated product (17.0 g, 0.071 mol) was dissolved in methyl formate (13.3 mL, 0.216 mol) and added dropwise to a sodium methoxide mixture prepared by adding sodium metal (1.79 g, 0.0778 g-atom) to tetrahydrofuran (325 mL) followed by slow addition of methanol (3.15 mL, 0.0778 mol). The combined mixture was stirred at room temperature for 18 hours, then evaporated to dryness. This crude product was dissolved in 50% aqueous methanol (200 mL), treated with charcoal, filtered and the solution was cooled in ice. Concentrated hydrochloric acid (14.3 mL of 12 N, 0.171 mol) was added slowly to this solution followed by a solution of potassium thiocyanate (8.6 g, 0.0885 mol) in water (20 mL). The mixture was heated in an oil bath held at 90° C. for 2.5 hours, then cooled to −10° C. The precipitated solid was filtered, washed with cold ethanol-water and dried at 60° C. to provide 14.7 g (74%) of 5-carboxymethyl-1-(2-chlorophenyl)methyl-2-thio-1H-imidazole; m.p. 72–74° C.

(ii) 1-(2-chlorophenyl)methyl-5-chloromethyl-2-propylthio-1H-imidazole

A mixture of 5-carboxymethyl-1-(2-chlorophenyl) methyl-2-thio-1H-imidazole(2 g, 7.08 mmol), ethyl acetate (20 mL), 5% sodium carbonate solution (40 mL) and propylbromide (4 mL, 44 mmol) was heated at 60° C. for 18 hours. The organic layer was separated, dried over magnesium sulfate and concentrated to 2.23 g of crude product. Trituration with diethyl ether provided 1.63 g (71%) of 5-carboxymethyl-1-(2-chlorophenyl)methyl-2-propylthio-1H-imidazole; m.p. 68–71° C. (from hexane).

The ester was hydrolyzed with aqueous sodium hydroxide solution to give 1-(2-chlorophenyl)methyl-2-thiopropyl-1H-imidazole-5-carboxylic acid; m.p. 158–159.5° C. (from ethanol).

A solution of 5-carboxymethyl-1-1-(2-chloro-phenyl) methyl-2-propylthio-1H-imidazole (3.74 g, 11.5 mmol) in dry tetrahydrofuran (50 mL) was cooled to −78° C. under argon, and a solution of diisobutyl aluminum hydride in toluene (30 mL of 1 M) was added dropwise. The mixture was stirred at −78° C. for 1.5 hours, then allowed to slowly warm to room temperature. The reaction was quenched by pouring onto iced dilute acetic acid, the product was extracted into methylene chloride and the organic extracts were washed with water, 5% sodium carbonate solution and brine. The dried, concentrated product was a light tan solid (3.32 g). Crystallization from ethanol/water gave 1-(2-chlorophenyl)methyl-5-hydroxymethyl-2-propylthio-1H-imidazole; m.p. 98–101° C.

A mixture of 1-(2-chlorophenyl)methyl-5-hydroxymethyl-2-propylthio-1H-imidazole (0.117 g, 0.393 mmol) in thionyl chloride (1 mL) was refluxed for 2 hours, evaporated in vacuo to an amorphous solid and triturated with ether to provide 1-(2-chlorophenyl)methyl-5-chloromethyl-2-propylthio-1H-imidazole hydrochloride (0.13 g, 94%).

(iii) 3-[(2-chlorophenyl)methyl]-2-propylthio-histidine ethyl ester

A solution of diisopropylamine (8.4 mL) in tetrahydrofuran (100 mL) was cooled to −78° C. under argon and a solution of n-butyl lithium (30 mL of 2.5 M in hexane) was added. The mixture was stirred at −78° C. for 30 minutes and at 0° C. for 10 minutes. After being recooled to −78° C., a solution of N-(diphenylmethylene)-glycine ethyl ester (Tetra. Lett., (1978), 2541, 4625) (15.4 g) in tetrahydrofuran (50 mL) was added, the mixture was stirred for 1 hour at −78° C. and a solution of 1-(2-chlorophenyl)methyl-5-chloromethyl-2-propylthio-1H-imidazole hydrochloride (9.4 g) in dry dimethylformamide (20 mL) was added. The mixture was then stirred at ambient temperature for 18 hours, poured into saturated ammonium chloride solution and the aqueous layer was extracted with methylene chloride. The organic extracts were washed with water, dried with magnesium sulfate concentrated and chromatographed over silica gel with 1% methanol in methylene chloride to afford 6.88 g of 3-[(2-chlorophenyl)methyl]-2-propylthio-N-(diphenylmethylene)histidine ethyl ester. This product (2.59 g) was dissolved in methylene chloride (52 mL), aqueous 1N hydrochloric acid solution (52 mL) was added and the mixture was stirred at 25° C. for 18 hours. The aqueous layer was separated, neutralized to pH 10.5 with sodium carbonate and the product was extracted into methylene chloride. The organic extract was dried with magnesium sulfate and concentrated to give 1.29 g (71%) of 3-[(2-chlorophenyl)methyl]-2-propylthio-histidine ethyl ester as an oil.

(iv) 3-[(2-chlorophenyl)methyl]-2-propylthio-N- butyrylhistidine ethyl ester

A solution of 3-(2-chlorophenyl)methyl-2-propylthiohistidine ethyl ester (0.4 g, 1.05 mmol) in methylene chloride (20 mL) was treated with triethylamine (0.17 mL) and butyryl chloride (0.12 mL). The mixture was stirred at 25° C. for 18 hours. The reaction was partitioned between ethyl acetate and water, and the organic layer was washed with water, dried, concentrated and chromatographed over silica gel with 1 to 3% of methanol in methylene chloride to give 0.367 g (77%) of 3-[(2-chlorophenyl)methyl]-2-propylthio-N-butyrylhistidine ethyl ester as an oil.

(v) 3-(2-chlorobenzenemethyl)-2-propylthio-N-butyrylhistidine

A mixture of 3-[(2-chlorophenyl)methyl-2-propylthio-N-butyrylhistidine ethyl ester (0.37 g, 0.819 mmole), ethanol (4 mL), water (4 mL) and potassium hydroxide pellets (0.098 g, 1.75 mmole) was stirred at 25° C. for 1 hour. The reaction was then diluted with water and the pH was adjusted to 4 with 1N aqueous hydrochloric acid solution. The product was extracted into methylene chloride, washed with water, dried and concentrated to an orange solid. Two crystallizations from chloroform provided 0.22 g of 3-[(2-chlorophenyl)methyl]-2-propylthio-N-butyrylhistidine; m.p. 178°–181° C.

The procedure of Example 2 is illustrative of the synthesis of compounds encompassed by generic formula (III).

EXAMPLE 2

3-[2-n-Butyl-1-{(2-chlorophenyl)methyl}-1H-imidazol-5-yl]-2-benzylpropanoic Acid (i) 2-n-butyl-1-(2-chlorophenyl)methyl-1H-imidazole Imidazole was converted to the 1-diethoxyortho-amide derivative by the method of Curtis and Brown, J. Org. Chem., (1980), 45, 20. Imidazole (12.8 g, 0.19 mol) and 118.4 g (0.8 mol) of triethylorthoformate were reacted in the presence of 1 g of p-toluenesulfonic acid to give 20.6 (61%), bp 65–70° C. (0.1 mm) of 1-diethoxyorthoamide imidazole. This product (24.0 g, 0.14 mol) was dissolved in dry tetrahydrofuran (250 mL), cooled to −40° C. and n-butyl lithium (0.14 mol, 56.4 mL of 2.5 M in hexane) was added at −40° C. to −35° C. After 15 minutes n-butyl iodide (31.1 g, 0.169 mol) was added at −40° C., and the reaction was stirred overnight at ambient temperature. The reaction was partitioned between ether and 0.3 N hydrochloric acid, and the organic layer was repeatedly extracted with dilute hydrochloric acid. The combined aqueous extracts were neutralized with sodium bicarbonate solution, extracted with methylene chloride, dried over magnesium sulfate and concentrated. A flash distillation on a Kugelrohr apparatus provided 14.8 g (85%) of 2-n-butylimidazole.

2-n-Butylimidazole (9.7 g, 0.078 mol) was dissolved in methanol (50 mL) and added dropwise to a solution of. sodium methoxide (from sodium hydride (2.31 g, 0.0934 mol) in methanol (250 mL)). After one hour the solution was evaporated to dryness, and the sodium salt was taken up in dry dimethylformamide (150 mL) and 2-chlorobenzyl bromide (16.3 g, 0.079 mol) was added. The mixture was heated at 50° C. for 17 hours under argon, poured onto ice water and the product was extracted into ethyl acetate. The extract was washed, dried, and concentrated to give 18.5 g of crude product which was chromatographed over silica gel with 2:1 ethyl acetate/hexane to provide 11.9 g (61%) of 2-n-butyl-1-(2-chlorophenyl)methyl-1H-imidazole as an oil. Thin layer chromatography on silica gel with 4:1 ethyl acetate/hexane gave an $R_f$ value of 0.59.

(ii) 2-n-butyl-1-(2-chlorophenyl)methyl-5-hydroxymethyl-1H-imidazole

Method 1

A mixture of 2-n-butyl-1-(2-chlorophenyl)methyl-1H-imidazole (95.5 g, 0.384 mol), 37% formaldehyde (500 mL), sodium acetate (80 g) and acetic acid (60 mL) was heated to reflux for 40 hours under argon. The reaction was concentrated in vacuo, and the residue was stirred with 500 mL of 20% sodium hydroxide solution for 4 hours, diluted with water and extracted with methylene chloride. The extract was washed, dried, and concentrated. The crude product (117 g) was flash chromatographed over 600 g of silica gel with a gradient of ethyl acetate to 10% of methanol in ethyl acetate to give 8.3 g of starting material, 24.5 g of a mixture of starting material and product, and 44 g (41%) of 2-n-butyl-1-(2-chlorophenyl)methyl-5-hydroxymethyl-1H-imidazole; mp 86–88° C. (from ethyl acetate). Further elution provided the bis (4,5-hydroxymethyl) derivative; mp 138–140° C. (from ethyl acetate).

Method 2

A mixture of valeramidine methyl ether hydrochloride (250 g, 1.66 mol) and dihydroxyacetone (150 g, 0.83 mol) dissolved in liquid ammonia was allowed to stand overnight at room temperature in a pressure vessel, and then heated at 65° C. for 4 hours at 375 psi. The ammonia was allowed to evaporate, and the residue was dissolved in methanol (3L). The resulting slurry was refluxed with added acetonitrile (1L). The solution was decanted from the solid ammonium chloride while hot. This procedure was repeated, and the combined acetonitrile extracts were treated with charcoal, filtered hot and the filtrate was concentrated in vacuum to give the dark oil, 2-n-butyl-5-hydroxymethylimidazole (253 g, 1.63 mol, 98%).

This crude alcohol (253 g) was treated with acetic anhydride (400 mL) at −15° C. and then was allowed to warm to ambient temperature with stirring, and then stirred an additional 19 hours. The acetic anhydride was evaporated at reduced pressure, the residue taken up in methylene chloride, and the organic phase was washed with 5% sodium bicarbonate solution and water. The extract was dried over sodium sulfate and concentrated to give 323 g (83%) of 1-acetyl-4-acetoxymethyl-2-n-butylimidazole.

This diacetate was N-alkylated by the following procedure. To a solution of triflic anhydride (120 mL, 0.71 mol) in methylene chloride (200 mL) at −78° C. under argon was added a solution of diisopropyl ethylamine (128 mL, 0.73 mol) and 2-chlorobenzyl alcohol (104 g, 0.72 mol) in methylene chloride (350 mL) over a period of 20 minutes.

After being stirred an additional 20 minutes at −78° C., this solution was then treated with 1-acetyl-4-acetoxymethyl-2-n-butylimidazole (146 g, 0.61 mol) dissolved in methylene chloride (300 mL) over a 20-minute interval. The mixture was then stirred at ambient temperature for 18 hours and the solvents were evaporated, The residual 2-n-butyl-5-acetoxymethyl-1-(2-chlorophenyl)methyl-1H-imidazole was used without purification for the hydrolysis of the acetate group.

A solution of crude 2-n-butyl-5-acetoxymethyl-1-(2-chlorophenyl)methyl-1H-imidazole (250 g) in methanol (200 mL) was treated with 10% sodium hydroxide solution (700 mL) and the mixture was heated on a steam bath for 4 hours. After cooling, methylene chloride was added, the organic phase was separated, washed with water, dried and concentrated. The residue was dissolved in ether, cooled, and seeded to give the crude product. Recrystallization from ethyl acetate gave 176 g of 2-n-butyl-1-(2-chlorophenyl) methyl-5-hydroxymethyl-1H-imidazole; mp 86–88° C. This material was identical in all respects to the product prepared by Method 1.

(iii) 2-n-butyl-2-(2-chlorophenyl)methyl-5-chloromethyl-1H-imidazole

A mixture of 2-n-butyl-1-(2-chlorophenyl)methyl-5-hydroxymethyl-1H-imidazole, prepared in Example 1 (ii), (10 g, 0.0337 mol) in thionyl chloride (75 ml) was refluxed for one hour, evaporated in vacuo and the residue azeotroped three times with toluene. The solid was triturated with ethyl ether and collected to provide 10.4 g (88%) of the hydrochloride salt of 2-n-butyl-1-(2-chlorophenyl)methyl-5-chloromethyl-1H-imidazole.

(iv) diethyl [2-n-butyl-1-{(2-chlorophenyl)methyl}-1H-imidazol-5-yl]-2-benzylmalonate To dry dimethylformamide (50 mL) under argon was added sodium hydride (0.53 g, 0.022 mol) followed by diethyl benzyl malonate (5.51 g, 0.022 mol) in dimethylformamide (10 mL) at 0° C. The mixture was stirred at ambient temperature for one hour. A solution of 2-n-butyl-1-(2-chlorophenyl)methyl-5-chloromethyl-1H-imidazole hydrochloride (3.5 g, 0.0105 mol) in dimethylformamide (40 mL) was added over 5 minutes. The reaction mixture was stirred at 25° C. for 18 hours, then partitioned between water and methylene chloride. The organic layer was washed with water, dried, and concentrated. The crude product was flash chromatographed over silica gel to give 4.54 g (85%) of the title compound as an oil.

(v) 3-[2-n-butyl-1-{(2-chlorophenyl)methyl}-1H-imidazol-5-yl]-2-benzylpropanoic acid A mixture of diethyl [(2-n-butyl-1-{(2-chlorophenyl) methyl}-1H-imidazol-5-yl]methyl-2-benzylmalonate (0.72 g, 1.36 mmol), potassium hydroxide (0.83 g, 14.7 mmol), water (15 mL) and ethanol (25 mL) was refluxed for 4 hours. The ethanol was evaporated, the residual aqueous layer was extracted with diethyl ether, and the basic solution was adjusted to pH 3.75 with concentrated hydrochloric acid. The precipitated product was extracted into methylene chloride, dried, and concentrated. This crude product was flash chromatographed on silica gel with 10% methanol in methylene chloride to give 0.51 g (86%) of 3-[2-n-butyl-1-{(2-chlorophenyl)methyl}-1H-imidazol-5-yl]-2-benzylpropanoic acid; mp 118–120° C. (from acetone/diethyl ether as the hydrochloride salt).

The procedure of Example 3 is illustrative of the synthesis of compound encompassed by generic formula (IV).

EXAMPLE 3

3-[2-n-Butyl-1-{(2-chlorophenylmethyl}-1H-imidazol-5-yl]benzoic Acid (i) 2-n-butyl-1-(trimethylsilyl)ethoxymethyl-imidazole Hexane-washed 80% sodium hydride (1.45 g, 0.0483 mol) in dimethylformamide (80 mL) under argon was treated with a solution of 2-n-butylimidazole (5.45 g, 0.0439 mol) in dimethylformamide (14 mL) dropwise at 25° C. and the reaction was stirred an additional hour. Then 2-(trimethylsilyl)ethoxymethyl chloride (SEM-Cl) (7.68 g, 0.0461 mol) was added, the mixture was stirred for 18 hours at ambient temperature and then partitioned between ice water and ethyl acetate. The washed, dried, concentrated organic solution was chromatographed over silica gel with 1:1 hexane in ethyl acetate to yield 10.8 g (96%) of 2-n-butyl-1-(trimethylsilyl)ethoxymethyl-imidazole.

(ii) 2-n-butyl-5-tributyltin-1-(trimethylsilyl) ethoxymethylimidazole

A solution of 2-n-butyl-1-SEM imidazole (prepared above) (6.37 g, 0.025 mol) in ethyl ether (125 mL) was treated dropwise with n-butyl lithium (0.0255 mol, 10.2 mL of 2.5 M in hexane) under argon at room temperature. After being stirred for an additional 45 minutes, tributyltin chloride (8.83 g, 7.4 mL, 0.026 mol) was added dropwise. The suspension was stirred overnight, saturated ammonium chloride solution was added and the ether layer was separated, washed with brine, dried over sodium sulfate, concentrated and flash chromatographed over silica gel with 3:1 hexane/ethyl acetate to provide 11.3 g (83%) of 2-n-butyl-5-tributyltin-1-(trimethylsilyl)ethoxymethylimidazole.

(iii) methyl 3-trifluoromethanesulfonyloxy-benzoate

To a solution of methyl 3-hydroxybenzoate (1.73 g, 11.3 mmol), 4-dimethylaminopryridine (215 mg, 1.74 mmol), and 2,6-lutidine (2.0 mL, 16.6 mmol) in 60 mL of methylene chloride at −30° C. was added trifluoromethane-sulfonic anhydride (2.8 mL, 16.6 mmol). After stirring the reaction mixture for 10 min at −30° C., the cooling bath was removed and the reaction was stirred at ambient temperature for 4 hours. Saturated aqueous ammonium chloride solution was then added, the layers were separated and the aqueous layer was back extracted twice with methylene chloride. The combined organic extracts were dried with sodium sulfate and the methylene chloride was removed in vacuo. The residue was dissolved in ethyl acetate and washed with water, 10% aqueous hydrochloric acid solution, saturated sodium bicarbonate solution and brine. The organic extract was dried with magnesium sulfate and the solvent was removed in vacuo. The crude product was flash chromatographed over silica gel eluting with 1:1 diethyl ether/hexane to give 3.13 (98%) of methyl 3-trifluoromethanesulfonyloxybenzoate.

(iv) methyl 3-[2-n-butyl-1-{(trimethylsilyl)ethoxymethyl}-1H-imidazol-5-yl]benzoate To a solution of 2-n-butyl-5-tributytin-1-(trimethylsilyl) ethoxymethylimidazole (6.06 g, 11.1 mmol), methyl 3-trifluoromethanesulfonyloxybenzoate (3.13 g, 11.0 mmol) in 53 mL of 1,4-dioxane at room temperature was added tetrakis(triphenylphosphine)palladium (0) (256 mg, 0.22 mmol). The reaction mixture was stirred under argon at room temperature for 10 minutes and then 2,6-di-t-butyl-4-methylphenol (10 mg) was added. The reaction was heated at 100° C. for 3.5 hours, cooled to room temperature and treated with 70 mL of diethyl ether and 65 mL of aqueous potassium fluoride solution. The reaction mixture was left stirring at room temperature for 17 hours and then filtered through Celite®. The organic layer was washed with water and brine, dried over magnesium sulfate and concentrated in vacuo. The crude product was flash chromoatgraphed over silica gel eluting with 3:1 ethyl aetate/hexane to give 2.88 g (67%) of methyl 3-[2-n-butyl-1-{(trimethylsilyl) ethoxymethyl}-1H-imidazol-5-yl]benzoate.

(v) methyl 3-[2-n-butyl-1-t-butoxycarbonyl-1H-imidazol-5-yl]benzoate

To a solution of methyl 3-[2-n-butyl-1-{(trimethylsilyl) ethoxymethyl}-1H-imidazol-5-yl]benzoate (2.88 g, 7.41 mmol) in 35 mL of ethanol was added 35 mL of 5N aqueous hydrochloric acid solution. The reaction mixture was heated at 55° C. for 25 hours and then an additional 20 mL of 5N aqueous hydrochloric acid solution was added. The reaction mixture was heated at 70° C. for one hour and then stirred at room temperature for 66 hours. The ethanol was removed in vacuo and the resulting aqueous layer was neutralized with saturated aqueous sodium bicarbonate solution and extracted with ethyl acetate. The organic extract was dried with sodium sulfate and the solvent was removed in vacuo.

The residue (1.46 g, 5.65 mmol) was dissolved in methanol (40 mL) and was treated with triethylamine (5.2 mL, 37.3 mmol) and di-t-butyl dicarbonate (8.4 mL, 35.4 mmol) at room temperature for 42.5 hours. The mixture was concentrated in vacuo and the crude product was flash chromatographed over silica gel with a gradient of ethyl acetate in hexane (1:8 to 4:1) to give 800 mg (30%) of methyl 3-[2-n-butyl-1-t-butoxycarbonyl-1H-imidazol-5-yl] benzoate.

(vi) methyl (3-[2-n-butyl-1-{(2-chlorophenyl)methyl}-1H-imidazol-5-yl]benzoate

To a stirred solution of trifluoromethanesulfonic anhydride (0.72 mL, 5.1 mmol) in methylene chloride (20 mL) held at −78° C. under argon was added a solution of 2-chlorobenzyl alcohol (748 mg, 5.25 mmol) and diisopropylethylamine (810 mg, 6.26 mmol) in methylene chloride (25 mL). After stirring for 15 minutes at −78° C., a solution of methyl (3-[2-n-butyl-1-t-butoxycarbonyl-1H-imidazol-5-yl]benzoate (1.53 g, 4.26 mmol) in methylene chloride (10 mL) was added dropwise over 10 minutes and the mixture was stirred overnight at room temperature. A solution of 5% sodium bicarbonate solution was added with stirring and the layers were separated, washed and dried. The reaction mixture was evaporated to dryness, the residue triturated with 1:1 hexane/ethyl acetate, the solid filtered off and the filtrate was concentrated and flash chromatographed over silica gel with 1:1 hexane/ethyl acetate to provide 600 mg (38%) of methyl (3-[2-n-butyl-1-{(2-chlorophenyl)methyl}-1H-imidazol-5-yl]benzoate.

(vii) 3-[2-n-butyl-1-{(2-chlorophenyl)methyl}-1H-imidazol-5-yl]benzoic acid

Methyl 3-[2-n-butyl-1-{(2-chlorophenyl)methyl}-1H-imidazol-5-yl]benzoic (600 mg, 1.63 mmol) was dissolved in 6 mL of ethanol and then 2 mL of 10% aqueous sodium hydroxide solution was added. The reaction mixture was stirred at room temperature overnight, 10% aqueous hydrochloric acid solution was added to pH 3.5 and the resulting solid was filtered, washed with water and dried to give 125 mg (21%) of 3-[2-n-butyl-1-}(2-chlorophenyl)methyl}-1H-imidazol-5-yl]benzoic acid as the hydrochloride salt; mp 200–202° C.

The procedures of Example 4 is illustrative of the synthesis of compounds encompassed by generic formula (V).

EXAMPLE 4

5-Bromo-2-n-butyl-1-(2-chnorophenyl)methyl-1H-benzimidazole-7-carboxylic Acid (i) 2,5-dibromo-3-nitrobenzoic acid The procedure described in R. K. Bentley and F. G. Holliman, J. Chem. Soc. (c), 2447 (1970) was used. A mixture of 2,5-dibromobenzoic acid (50 g, 0.18 mol) in concentrated sulfuric acid was vigorously stirred as fuming nitric acid (62.5 mL) was added dropwise at a rate to keep the temperature below 70° C. The reaction mixture was vigorously stirred, heated to 100° C. and then kept at 100° C. for 5 hours. The cooled reaction was cautiously poured into 2 liters of ice and vigorously stirred, the precipitate was filtered through a sintered glass funnel and the solid was washed well with water. Crystallization was achieved by dissolving the solid in acetic acid (150 mL) and after concentration to a half of the volume, crystals separated (16.72 g); mp 225–229° C. An additional crop of 7.52 g was obtained to give a total yield of 24.24 g (41%).

(ii) 5-bromo-2-[(2-chlorophenyl)methyl]amino-3-nitrobenzoic acid

A suspension of 2,5-dibromo-3-nitrobenzoic acid (10.76 g, 0.0331 mol) in toluene (100 mL) was placed under argon, treated with 2-chlorobenzylamine (14.06 g, 0.0993 mol) and the mixture was brought to reflux. A clear, red solution resulted and the solution was refluxed for 24 hours, cooled, poured into 5% sodium hydroxide solution (600 mL) and ether (100 mL). The insoluble material was filtered off, the layers separated and the aqueous phase was added to the insoluble material and acidified with 10% hydrochloric acid solution. The separated crystalline product was collected, washed with water and the solid was crystallized from a large volume of methanol to provide 7.85 g (61.5%) of the yellow crystalline 5-bromo-2-[(2-chlorophenyl)methyl] amino-3-nitrobenzoic acid; mp 159–161° C.

(iii) 5-bromo-2-[(2-chlorophenyl)methyl-N-valeryl]amino-3-nitrobenzoic acid

A solution of 5-bromo-2-[(2-chlorophenyl)methyl]-amino-3-nitrobenzoic acid (8 g, 0.021 mmol) in pyridine (100 mL) was cooled in ice under argon and valeryl chloride (5.5 g, 0.046 mol) was added. The mixture was heated at 45° C. for 18 hours, poured into water, acidified with hydrochloric acid and the oily product was extracted into ethyl acetate. The organic extracts were washed with 10% hydrochloric acid solution and brine, and the dried, concentrated product afforded about 100% yield of the crude oil, 5-bromo-2-[(2-chlorophenyl)methyl-N-valeryl]-amino-3-nitrobenzoic acid, which was used without further purification.

(iv) 5-bromo-2-n-butyl-1-(2-chlorophenyl)methyl-1H-benzimidazole-7-carboxylic acid A solution of 5-bromo-2-[(2-chlorophenyl)methyl-N-valeryl]amino-3-nitrobenzoic acid (9.72 g, 0.0207 mol) in tetrahydrofuran (75 mL) was diluted with 5% sodium bicarbonate solution (75 mL), and then treated portionwise with sodium hydrosulfite (12 g) over 2 hours. The pH was adjusted to 7.1 with additional solid sodium bicarbonate. After an hour of stirring, 6 g of additional sodium hydrosulfite was added, and, after another hour of stirring, the mixture was filtered, diluted with ether, and the layers were separated. The organic phase was concentrated to a solid that was dissolved in acetic acid (15 mL) and concentrated hydrochloric acid (5 mL) and heated on a steam bath for 2 hours. The residual slurry was concentrated in vacuo, diluted with water and the solid was collected. The solid was dissolved in hot methanol, some insolubles filtered off, and the filtrate was concentrated to incipient crystallization. After chilling, there was obtained 4.26 g (37%) of 5-bromo-2-n-butyl-1-(2-chlorophenyl)methyl-1H-benzimidazole-7-carboxylic acid; mp 254–255° C.

EXAMPLE 5

An oral dosage form for administering orally active Formula (I) compounds is produced by screening, mixing and filling into hard gelatin capsules the ingredients in proportions, for example, as shown below.

| Ingredients | Amounts |
| --- | --- |
| (E)-3-[2-n-butyl-1-{(4-carboxy-phenyl)methyl}-1H-imidazol-5-yl]-2-(2-thienyl)methyl-2-propenoic acid | 100 mg |
| magnesium stearate | 10 mg |
| lactose | 100 mg |

EXAMPLE 6

The sucrose calcium sulfate dihydrate and orally active Formula (I) compounds are mixed and granulated with a 10% gelatin solution. The wet granules are screened, dried, mixed with the starch, talc and stearic acid, screened and compressed into a tablet.

| Ingredients | Amounts |
| --- | --- |
| (E)-3-[2-n-propyl-1-{(4-carboxynaphth-1-yl)methyl}-1H-imidazol-5-yl]-2-(2-thienyl)methyl-2-propenoic acid | 75 mg |
| calcium sulfate dihydrate | 100 mg |
| sucrose | 15 mg |
| starch | 8 mg |
| talc | 4 mg |
| stearic acid | 2 mg |

EXAMPLE 7

(E)-3-[2-n-Butyl-1-{(4-carboxyphenyl)methyl}-1H-imidazol-5-yl]-2-(2-thienyl)methyl-2-propenoic acid, 50 mg, is dispersed in 25 ml of normal saline to prepare an injectable preparation.

It is to be understood that the invention is not limited to the embodiments illustrated hereabove and the right to the illustrated embodiments and all modifications coming within the scope of the following claims is reserved.

What is claimed is:

1. A method of treating diabetic nephropathy in a mammal which comprises administering to a subject in need thereof an effective amount of an angiotensin II receptor antagonist.

2. The method of claim 1 which comprises administering an angiotensin II receptor antagonist of the formula:

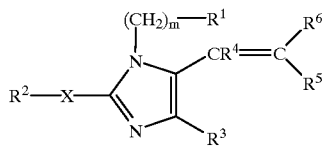

in which:

$R^1$ is adamantyl, phenyl, biphenyl, or naphthyl, with each aryl group being unsubstituted or substituted by one to three substituents selected from Cl, Br, F, I, $C_1$–$C_6$alkyl, nitro, A-$CO_2R^7$, tetrazol-5-yl, $C_1$–$C_6$alkoxy, hydroxy, $SC_1$–$C_6$alkyl, $SO_2NHR^7$, $NHSO_2R^7$, $SO_3H$, $CONR^7R^7$, CN, $SO_2C_1$–$C_6$alkyl, $NHSO_2R^7$, $PO(OR^7)_2$, $NR^7R^7$, $NR^7COH$, $NR^7COC_1$–$C_6$alkyl, $NR^7CON(R^7)_2$, $NR^7COW$, W, $SO_2W$;

m is 0–4;

$R^2$ is $C_2$–$C_{10}$alkyl, $C_3$–$C_{10}$alkenyl, $C_3$–$C_{10}$alkynyl, $C_3$–$C_6$cycloalkyl, or $(CH_2)_{0-8}$phenyl unsubstituted or substituted by one to three substituents selected from $C_1$–$C_6$alkyl, nitro, Cl, Br, F, I, hydroxy, $C_1$–$C_6$alkoxy, $NR^7R^7$, $CO_2R^7$, CN, $CONR^7R^7$, W, tetrazol-5-yl, $NR^7COC_1$–$C_6$alkyl, $NR^7COW$, $SC_1$–$C_6$alkyl, $SO_2W$, or $SO_2C_1$–$C_6$alkyl;

X is a single bond, S, $NR^7$, or O;

$R^3$ is hydrogen, Cl, Br, F, I, CHO, hydroxymethyl, $COOR^7$, $CONR^7R^7$, $NO_2$, W, CN, $NR^7R^7$, or phenyl;

$R^4$ and $R^5$ are independently hydrogen, $C_1$–$C_6$alkyl, thienyl-Y-, furyl-Y-, pyrazolyl-Y-, imidazolyl-Y-, pyrrolyl-Y-, triazolyl-Y-, oxazolyl-Y-, isoxazolyl-Y-, thiazolyl-Y-, pyridyl-Y-, or tetrazolyl-Y-, except that $R^4$ and $R^5$ are not both selected from hydrogen and $C_1$–$C_6$alkyl and each heterocyclic ring is unsubstituted or substituted by $C_1$–$C_6$alkyl, $C_1$–$C_6$alkoxy, Cl, Br, F, I, $NR^7R^7$, $CO_2R^7$, $SO_2NHR^7$, $SO_3H$, or $CONR^7R^7$, OH, $NO_2$, W, $SO_2W$, $SC_1$–$C_6$alkyl, $SO_2C_1$–$C_6$alkyl, $NR^7COH$, $NR^7COW$, or $NR^7COC_1$–$C_6$alkyl;

Y is a single bond, O, S, or $C_1$–$C_6$alkyl which is straight or branched or optionally substituted by phenyl or benzyl, wherein each of the aryl groups is unsubstituted or substituted by halo, $NO_2$, $CF_3$, $C_1$–$C_6$alkyl, $C_1$–$C_6$alkoxy, CN, or $CO_2R^7$;

$R^6$ is —Z—$COOR^8$ or —Z—$CONR^7R^7$;

Z is a single bond, vinyl, —$CH_2$—O—$CH_2$—, methylene optionally substituted by $C_1$–$C_6$alkyl, one or two benzyl groups, thienylmethyl, or furylmethyl, or —C(O)NHCHR$^9$—, wherein $R^9$ is H, $C_1$–$C_6$alkyl, phenyl, benzyl, thienylmethyl, or furylmethyl;

W is $C_nF_{2n+1}$, $C_nF_{2n+1}$, wherein n is 1–3;

A is —$(CH_2)_m$—, —CH=CH—, —O$(CH_2)_n$—, or —S$(CH_2)_n$—;

each $R^7$ independently is hydrogen, $C_1$–$C_6$alkyl, or $(CH_2)_m$ phenyl, wherein m is 0–4; and $R^8$ is hydrogen, $C_1$–$C_6$alkyl, or 2-di($C_1$–$C_6$alkyl)-amino-2-oxoethyl; or a pharmaceutically acceptable salt thereof.

3. The method of claim 2 wherein the angiotensin II receptor antagonist is (E)-3-[2-n-butyl-1-{4-carboxyphenyl)methyl}-1H-imidazol-5-yl]-²-(2-thienyl)methyl-2-propenoic acid or a pharmaceutically acceptable salt thereof.

4. The method of claim 3 wherein the angiotensin II receptor antagonist is (E)-3-[2-n-butyl-1-{(4- carboxyphenyl)methyl]-1H-imidazolyl-5-yl]-2-( 2-thienyl) methyl-2-propenoic acid methanesulfonate.

5. The method of claim 2 wherein the angiotensin II receptor antagonist is (E)-3-[2-n-butyl-1-{4-carboxynaphth-1-yl)methyl}-1H-imidazol-5-yl]-2-(2-thienyl)methyl-2-propenoic acid or a pharmaceutically acceptable salt thereof.

6. The method of claim 1 wherein the angiotenin II receptor antagonist is:

(E)-3-[2-n-butyl-1-{(4-carboxyphenyl)methyl]-1H-imidazol-5-yl]-2-n-butyl-2-propenoic acid;

(E)-1-[2-n-butyl-1-{(4-carboxyphenyl)methyl]-1H-imidazol-5-yl]-2-(1H-tetrazol-5-yl)-3-(2-thienyl)-1-propene; or N-[{1-(4-carboxyphenyl)methyl]-2-n-butyl-1H-imidazol-5-yl}methyl]-β-(2-thienyl)alanine; or a pharmaceutically acceptable salt thereof.

7. The method of claim 1 wherein the angiotensin II receptor antagonist 2-n-butyl-4-chloro-1-[(2'-(1H-tetrazol-5-yl) biphenyl-4-yl) methyl]-5-(hydroxymethyl)-imidazole or a pharmaceutically acceptable salt thereof.

8. The method of claim 1 wherein the angiotensin II receptor antagonist is 2-n-propyl-4-pentufluoroethyl-1-[2'-(1H-tetrazol-5-yl)biphenyl-4-yl)methyl]imidazole-5-carboxylic acid or a pharmaceutically acceptable salt thereof.

9. The method of claim 1 wherein the angiotensin II receptor antagonist is 5,7-dimethyl-2-ethyl-3-(2'-(tetrazol-5-yl)biphenyl-4-yl)methyl-3H-imidazo[4,5-b]pyridine or a pharmaceutically acceptable salt thereof.

10. The method of claim 1 wherein the angiotensin II receptor antagonist is 2-methyl-4-{(2'-(1H-tetrazol-5-yl) biphenyl-4-yl)methoxy]quinoline or a pharmaceutically acceptable salt thereof.

11. The method of claim 1 wherein the angiotensin II receptor antagonist is 2-n-butyl-4-chloro-1-{[3-bromo-2-[2-(tetrazol-5-yl)phenyl]benzofuranyl-4-yl]methyl}imidazole-5-acetic acid or a pharmaceutically acceptable salt thereof.

* * * * *

(12) REEXAMINATION CERTIFICATE (4762nd)
United States Patent
Hill

(10) Number: US 6,028,091 C1
(45) Certificate Issued: Apr. 8, 2003

(54) MEDICAMENT

(75) Inventor: James Hill, Brentford (GB)

(73) Assignee: SmithKline Beecham P.L.C., Brentford (GB)

Reexamination Request:
No. 90/006,148, Nov. 26, 2001

Reexamination Certificate for:
Patent No.: 6,028,091
Issued: Feb. 22, 2000
Appl. No.: 09/371,673
Filed: Aug. 10, 1999

Related U.S. Application Data

(63) Continuation of application No. 09/277,922, filed on Mar. 29, 1999, now abandoned, which is a continuation of application No. 08/901,460, filed on Jul. 28, 1997, now abandoned, which is a continuation of application No. 08/732,027, filed on Oct. 16, 1996, now abandoned, which is a continuation of application No. 08/535,796, filed on Sep. 28, 1996, now abandoned, which is a continuation of application No. 08/375,028, filed on Jan. 19, 1995, now abandoned, which is a continuation of application No. 08/074,870, filed as application No. PCT/GB91/02220 on Dec. 12, 1991, now abandoned.

(30) Foreign Application Priority Data

Dec. 14, 1990 (GB) .............................................. 9027210

(51) Int. Cl.[7] ........................ A61K 31/41; A61K 31/415
(52) U.S. Cl. ........................ 514/381; 514/382; 514/397; 514/398; 514/399; 514/400

(56) References Cited

U.S. PATENT DOCUMENTS

| | | | |
|---|---|---|---|
| 5,064,825 A | | 11/1991 | Chakravarty et al. |
| 5,066,586 A | * | 11/1991 | Chen et al. .................. 435/119 |
| 5,100,897 A | * | 3/1992 | Allen et al. .................. 514/269 |
| 5,102,880 A | * | 4/1992 | Chakravarty et al. ....... 514/212 |
| 5,164,407 A | * | 11/1992 | Greenlee et al. ............ 514/381 |
| 5,183,810 A | * | 2/1993 | Greenlee et al. .............. 514/63 |

FOREIGN PATENT DOCUMENTS

EP  0 400 835 A1  12/1990

\* cited by examiner

*Primary Examiner*—Fiona T. Powers

(57) ABSTRACT

The present invention relates to the use of an angiotensin II receptor antagonist in the manufacture of a medicament for the treatment of diabetic nephropathy.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 2–11 is confirmed.

Claim 1 is cancelled.

\* \* \* \* \*